United States Patent [19]
Meienhofer

[11] 4,238,390
[45] Dec. 9, 1980

[54] SYNTHESIS AND BIOLOGICAL ACTIVITY OF [D-Thr$^2$, $\Delta^3$Pro$^5$]-ENKEPHALINAMIDE

[75] Inventor: Johannes A. Meienhofer, Upper Montclair, N.J.

[73] Assignee: Hoffmann-La Roche Inc., Nutley, N.J.

[21] Appl. No.: 37,559

[22] Filed: May 9, 1979

[51] Int. Cl.$^3$ .................... C07C 103/52; A61K 37/00
[52] U.S. Cl. ............................ 260/112.5 R; 424/177;
[58] Field of Search ................. 260/112.5 R, 112.5 E; 424/177

[56] References Cited
PUBLICATIONS

Vizi; E. S., Biological Abst. 1978, p. 4879.
Szekely; J. I., Biological Abst. 1978, p. 23486.
Yamashiro et al., Biochem. and Biophys. Res. Commun. 78, 1977, 1124–1129.
Bajusz et al., Biochem. and Biophys. Res. Commun., 84, 1978, 1045–1053.

*Primary Examiner*—Delbert R. Phillips
*Attorney, Agent, or Firm*—Jon S. Saxe; Bernard S. Leon; James H. Callwood

[57] ABSTRACT

The present disclosure is directed to the synthesis and biological activity of [D-Thr$^2$, $\Delta^3$Pro$^5$]-enkephalinamide. The subject compound is useful as an agent for the inhibition of diarrhea and also exhibits analgesic activity.

2 Claims, No Drawings

SYNTHESIS AND BIOLOGICAL ACTIVITY OF [D-Thr², Δ³Pro⁵]-ENKEPHALINAMIDE

BACKGROUND OF THE INVENTION

1. Field of the Invention

This invention relates to the synthesis and biological activity of a novel enkephalin analog. More particularly, this invention is concerned with the synthesis and biological activity of [D-Thr², Δ³Pro⁵]-enkephalinamide.

2. Description of the Prior Art

The enkephalinamide compound [D-Met², Pro⁵]-enkephalinamide has been reported to be a potent analgesic agent by Bajusz et al., FEBS Letters 76,91 (1977).

It has been known in the art that proline can be replaced by thiazolidine-4-carboxylic acid (Thz) in biologically-active peptides. See, for example, Felix el al., Int. J. Pept. Prot. Res. 5, 201 (1973) and Rosamond and Ferger, J. Med. Chem. 19, 873 (1976).

Further, it is known that the 2-position in Met-enkephalin appears to be sensitive to the nature of the side chain. Hambrook et al., Nature (London) 262, 782 (1976); Pert et al., Science 194, 330 (1976); and Bajusz et al., Acta Biochim. Biophys. Acad. Sci., Hung. 11, 305 (1976).

Recently, Roemer et al., Nature 268, 547 (1977) have reported on several Met-enkephalin analogs, the most potent analgesic of the group being [D-Ala², MePhe⁴, MetO⁵-ol] enkephalin which was indicated to be orally active.

U.S. Patent No. 4,103,005 to Li describes the synthesis and biological activity of enkephalin analogs, [D-Met², Thz⁵]-enkephalinamide and [D-Thr², Thz⁵]-enkephalinamide, which are claimed to be potent analgesic agents. In accordance with the present invention, disclosed herein is [D-Thr², Δ³Pro⁵]-enkephalinamide, a potent agent for the inhibition of 5-hydroxytryptophan-induced diarrhea by intravenous injection.

SUMMARY OF THE INVENTION

An enkephalin analog having the following structure:

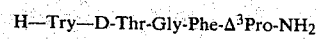

Detailed Description of the Invention

The analog of the present invention is readily prepared by solution phase and solid phase synthesis procedures well known in the art.

The solid phase synthesis procedures can proceed, for example, as described by Merrifield, J., Am. Chem. Soc., 85, page 2149 (1963). The resin support utilized in such procedures can be any conventional resin employed in solid phase synthesis such as a copolystyrenedivinylbenzene resin. The resin's terminal reactive site for coupling the first amino acid onto the resin can be halomethyl, such as bromo or chloromethyl, or hydroxymethyl. If such resin forms are used, then the resulting peptide product obtained after cleavage of the resin contains a carboxy terminal carboxyl group which must then be converted into the desired amide form by methods known per se. Suitable procedures for this purpose include formation of a lower alkyl ester, such as the methyl ester, followed by ammonolysis or by treatment of the carboxyl peptide with ammonia in the presence of dicyclohexylcarbodiimide. Alternatively, the desired peptide amide can be obtained by ammonolysis of the peptide resin.

[D-Thr², Δ³Pro⁵]-enkephalinamide can be preferably synthesized according to the claimed invention by solution phase synthesis procedures well known in the art. According to such procedures, an amino terminal dipeptide having the structure:

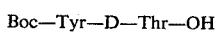

can be activated with a carbodiimide coupling agent such as dicyclohexylcarbodiimide (DCC) and 1-hydroxybenzotriazole (HOBt), and the ensuing active ester is reacted with the hydrochloride salt of a carboxyl terminal tripeptide having the structure:

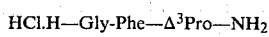

to yield the structure:

in protected form followed by removal of the protecting groups to yield the structure:

Removal of the protecting group from the above compound is readily accomplished by procedures known per se, such as, for example, by treatment with HCl in tetrahydrofuran.

Any conventional protecting group may be utilized in the synthesis of the subject compound. For example, benzyl, acetyl, benzoyl, tert-butyl, trityl, 4-bromobenzyl, 2,6-dichlorobenzyl, benzyloxycarbonyl, t-butyloxycarbonyl and the like.

The synthesis of the subject compound is illustrated by the following series of equations:

SYNTHESIS FLOW SCHEME
Example
Methods and Materials

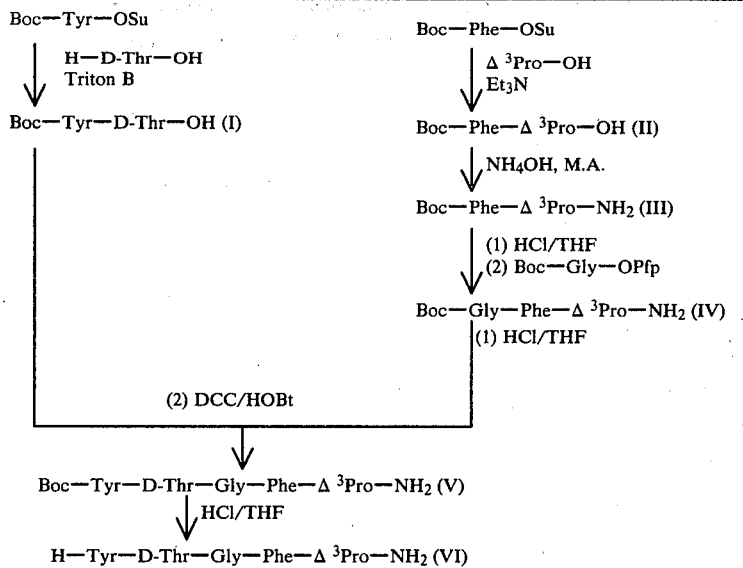

The compounds of the present invention are useful as antidiarrheal and analgesic agents. Suitable dosage regimens for this purpose include a parenteral dosage of from 0.1 to 100 mg/kg, more preferably from 1 to 10 mg/kg, which may be repeated as needed. The active compounds are most preferably formulated by passing an aqueous solution through a sterile filter to remove any bacterial contamination, lyophilizing the subdivided filtrate in vials containing the desired amount of compound and then reconstituting the lyophilized solid with sterile isotonic saline or distilled water prior to administration.

The preparation and biological activity of the analog of the present invention is further illustrated by the following examples:

Solution Phase Synthesis of [D-Thr$^2$, $\Delta^3$Pro$^5$]-Enkephalinamide

Boc-Tyr-D-Thr-OH (I)

D-Threonine (4.58 g, 38.5 mmol) was dissolved in 19 ml of 40% Triton B and evaporated to an oil. It was re-evaporated twice from DMF, and the salt obtained was stirred with Boc-Tyr-OSu (13.24 g, 35 mmol) in DMF (80 ml) at 0° C. for 1.5 hr and at 25° C. for 30 hr. A constant pH of 8 was maintained by dropwise addition of Et$_3$N during reaction time. The reaction was acidified to pH 4 with acetic acid. The solvent was evaporated to a syrup, dissolved in chloroform, washed with 0.5 N H$_2$SO$_4$ and water, dried (Na$_2$SO$_4$) and evaporated to low volume. The product was obtained as an amorphous solid from petroleum ether: 9.17 g (68.5%): $[\alpha]_D^{25}$-42.9° (c 1.4, DMF).

Anal. Calcd. for C$_{18}$H$_{26}$N$_2$O$_7$ (382.42): C, 56.53; H, 6.85; N, 7.32. Found: C, 56.67; H, 7.00; N, 7.10.

Boc-Phe- $\Delta^3$-Pro-OH (II)

A suspension of $\Delta^3$Pro-OH (1.19 g, 10.5 mmol) in DMF (10 ml) was stirred with Boc-Phe-OSu (3.62 g, 10 mmol) and Et$_3$N (1.4 ml, 10 mmol) at 0° C. for 1 hr and 25° C. for 24 hrs. During this time, a few drops of Et$_3$N was added to the reaction to maintain a pH between 7 and 8. The solvent was evaporated to an oily residue which was taken up into EtOAc. The organic phase was washed with 0.5 N H$_2$SO$_4$, H$_2$O, dried (Na$_2$SO$_4$), and the product was precipitated by addition of petroleum ether. Reprecipitation from EtOAc/petroleum ether, provided 3.06 g (85%); m.p. 151.5°-153.5° C.; $[\alpha]_D^{25}= -142.7°$ (c 2, EtOAc). Fine crystals were obtained from EtOAc.

Anal. Calcd. for C$_{19}$H$_{24}$N$_2$O$_5$ (360.417): C, 63.32; H, 6.71; N, 7.77. Found: C, 63.54; H, 6.70; N, 7.72.

Boc-Phe-$\Delta^3$Pro-NH$_2$ (III)

Compound II (9.0 g, 25 mmol) was dissolved in THF (25 ml) and stirred at $-10°$ C. with Et$_3$N (3.85 ml) and i-butylchloroformate (3.62 ml) for 3.5 min. NH$_4$OH (5 ml) was added, and the reaction mixture stirred at $-10°$ C. for 0.5 hr and 25° C. for 3 hr. The solution was evaporated to a syrup, dissolved in EtOAc and washed with 1.5 N H$_2$SO$_4$, water, 5% NaHCO$_3$, water. The organic phase was dried (Na$_2$SO$_4$) and evaporated to a low volume from which crystalline product was obtained with addition of petroleum ether: 8.0 g (89%).

Anal. Calcd. for C$_{19}$H$_{25}$N$_3$O$_4$ (359.43): C, 63.49; H, 7.01; N, 11.69. Found: C, 63.51; H, 6.79; N, 11.63.

Boc-Gly-Phe-$\Delta^3$Pro-NH$_2$ (IV)

Compound III (5.39 g, 15 mmol) was treated with 4 N HCl in THF (182 ml) for 0.5 hr. Evaporation of the excess HCl and solvent and treatment with dry ether afforded an amorphous solid. The HCl salt was dissolved in DMF and stirred with Et$_3$N (2.1 ml) and Boc-Gly-OPfp (5.37 g, 15.75 mmol) at 0° C. for 1.5 hr and 25° C. for 1.5 hr. During this time, some additional Et$_3$N was added occasionally to maintain pH 7. The reaction mixture was evaporated to a small volume to which was added EtOAc and N,N-dimethylaminoethylamine (1.1 ml). After 5 min, the reaction mixture was extracted with 10% citric acid, 0.5 N H$_2$SO$_4$, water and 5% NaHCO$_3$. After drying (Na$_2$SO$_4$) and evaporation to a smaller volume, precipitation by hexane provided 4.06 g (65%) of compound V.

Compound V was also provided through the mixed anhydride (Boc-Gly-OH) procedure: colorless powder.

Anal. Calcd. for C$_{21}$H$_{28}$N$_4$O$_5$ (416.487): C, 60.56; H, 6.78; N, 13.45. Found: C, 60.65; H, 6.88; N, 13.14.

Boc-Tyr-D-Thr-Gly-Phe-$\Delta^3$Pro-NH$_2$ (V)

Compound IV (0.46 g, 1.1 mmol) was treated with 4 N HCl in THF (13.75 ml) for 30 min; during this time, the salt started to precipitate. It was worked up as usual to provide 0.37 g (95.6%) of the HCl salt.

Boc-Tyr-D-Thr-OH (I) (0.42 g, 1.1 mmol) was dissolved in DMF (3 ml), and the solution was cooled to 0° C. HOBt (0.34 g, 2.2 mmol) was added, and then DCC (0.25 g, 1.21 mmol) and the mixture was kept stirring at 0° C. for 1.5 hrs and 25° C. for 1 hr. The mixture was then cooled to 0° C., and the above-described HCl salt (0.35 g, 1 mmol) was added and NMM* to pH 8. The reaction mixture was stirred at 0° C. for 1 hr and 25° C. for 2 days, while the pH was kept between 7 and 8 by addition of NMM. The precipitated by-products were filtered off, the filtrate was evaporated after acidification to pH 5 with glacial AcOH. The residue was taken up into EtOAc, and the EtOAc phase was washed with 0.5 N H$_2$SO$_4$, H$_2$O, 5% NaHCO$_3$, H$_2$O, dried (Na$_2$SO$_4$) and evaporated to a smaller volume. Precipitation by ether provided 0.36 g (53.2%) of compound V, $[\alpha]_D^{25} = -61.8°$ (c 1, EtOH).
*NMM=N-methylmorpholine Anal. Calcd. for C$_{34}$H$_{44}$N$_6$O$_9$ (680.774): C, 59.99; H, 6.52; N, 12.34. Found: C, 59.59; H, 6.64; N, 11.95.

Amino Acid Analysis (6 N HCl, anisol, 110° C.): $\Delta^3$Pro$_{1.15}$, Thr$_1$, Gly$_1$, Tyr$_{1.098}$, Phe$_{0.96}$.

[D-Thr$^2$, $\Delta^3$Pro$^5$]-Enkephalinamide (VI)

Compound V (0.82 g, 1.2 mmol) was stirred in 3.75 N HCl in THF (20 ml) for 25 min. The HCl salt of the product precipitated out of solution after just a few min. After evaporation of the excess HCl and solvent and treatment with dry ether, an amorphous solid, 0.68 g (92.5%), was obtained.

A portion (53 mg) was subjected to reversed-phase HPLC chromatography on a 44×3.7 cm column (E. Merck LiChroprep RP-8) equilibrated with 0.01 M trifluoroacetic acid and eluted with a linear gradient to 10% acetonitrile in 0.01 M trifluoroacetic acid. (UV detection at 225 nm). Fractions from the major product peak were pooled, lyophilized and passed down a Sephadex G-10 column, 2.5×100 cm, with 0.01 M HCl as eluting buffer. Lyophilized fractions from a single symmetrical peak afforded the product: 35 mg (66%).

Amino Acid Analysis: $\Delta^3$Pro$_{0.96}$, Thr$_{1.00}$, Gly$_{0.98}$, Tyr$_{1.06}$, Phe$_{0.99}$, NH$_3^{1.02}$, $[\alpha]_D^{25} = -29.36°$ (c 0.1, 0.1 N HCl).

Anal. Calcd. for C$_{29}$H$_{37}$N$_6$O$_7$Cl$_1$ (617.1): C, 56.44; H, 6.04; N, 13.62; Cl, 5.74. Found: C, 56.33; H, 6.26; N, 13.48; Cl, 5.85.

Solid Phase Synthesis of [D-Thr$^2$, $\Delta^3$Pro$^5$]-Enkephalinamide (VII)

Benzhydrylamine (BHA) resin (4.7 g) was placed in a glass reaction vessel of a peptide synthesizer. Methylene chloride (40 ml) was added, followed by Boc-$\Delta^3$Pro-OH (0.86 g). After mixing (10 min), dicyclohexylcarbodiimide (0.83 g) was added. After 2 hours of mixing, the solvent was removed and the resin washed with methylene chloride (2×25 ml). Complete coupling was indicated by a negative ninhydrin test. Boc cleavage was effected by treatment with 50% trifluoroacetic acid in methylene chloride (50% TFA, 30 ml) for 30 min. The resin was washed for 1 min each with 30 ml volumes of methylene chloride, methanol and methylene chloride. After treatment with 10% triethylamine in methylene chloride (2×5 min, 30 ml each) and washing with methylene chloride (2×30 ml), the resin was ready for the next cycle.

Incorporation of Boc-Gly-Phe-OH, Boc-DThr(Bzl)-OH and Boc-Tyr(tBu)-OH was effected as described above. The resin was dried in a vacuum oven (yield, 7.2 g). A sample of peptide resin (1 g) was treated with anhydrous hydrogen fluoride for 45 min at 0° C. in a teflon reaction vessel. After removal of the HF at room temperature under reduced pressure, the residue was triturated with EtOAc (4×50 ml) and filtered. The peptide was extracted by 5 successive treatments of the solid with glacial acetic acid (10 ml each). The combined extracts were lyophilized to yield a crude product (1.1 g) as an amorphous solid. RP-8 reverse phase HPLC chromatography followed by Sephadex G-10 gel filtration as described above (for compound VI) proviced purified [D-Thr$^2$, $\Delta^3$Pro$^5$]enkephalinamide (0.5 g).

Anti-Diarrhea Activity of [D-Thr$^2$, $\Delta^3$Pro$^5$]-Enkephalinamide in CF-1 Mice Compound

[2-D-threonine, 5-(3,4-dehydroproline)]-enkephalinamide

Procedure

Male CF-1 mice were used. The mice were housed at least one week prior to use. At the time of use, the mice were 49 days of age and weighed between 21-25 grams. The mice received, intravenously, vehicle, or the indicated amounts of, [D-Thr$^2$, $\Delta^3$Pro$^5$]enkephalinamide dissolved in sterile 0.9% sodium chloride. Thirty seconds later, 10 mg/kg of DL-5-hydroxytryptophan was administered intraperitoneally using distilled water as the vehicle. The mice were then immediately placed in individual open-bottomed wire cages resting on pre-weighed parafilm sheets. The mice were removed from their cages 30 minutes after receiving the DL-5-hydroxytryptophan. Any fecal material adhering to the sides of the wire cage was collected and placed on the parafilm sheets, and any visible urine on the sheets was blotted dry. The sheets were weighed, and the weight increment was considered to represent the amount of feces discharged during the 30-minute test period.

The percent inhibition of diarrhea was calculated by determining the percentage decrease in fecal weight of [D-Thr$^2$, $\Delta^3$Pro$^5$]-enkephalinamide-treated animals following 5-hydroxytryptophan in comparison to those also receiving 5-hydroxytryptophan but pretreated with vehicle (0.9% sodium chloride). The anti-diarrhea ED50 values were determined using a computer program "ED50" based on the probit method of D. J. Finney, "Probit Analysis", Cambridge University Press, Cambridge, Great Britain (1971). The average percent inhibition obtained at each dose level of [D-Thr$^2$, $\Delta^3$Pro$^5$]-enkephalinamide was used as the response.

Results

The results of this study are shown in Table I and are compared with the antidiarrhea activity of morphine sulfate, human β-endorphin and the indicated enkephalin analogs. The comparative tests were carried out using male CD-1 mice according to the following procedure:

MATERIALS AND METHODS

Male CD-1 mice were obtained from Charles River, Inc., Wilmington, Massachusetts, and weighted between 18 and 25 grams at the time of use.

All compounds with the exception of 5-HTP were dissolved in sterile 0.9% sodium chloride solution. Distilled water was used as the vehicle for 5-HTP. All compounds were administered to the mice using a constant dosage volume of 0.2 ml/20 gms of body weight.

The endorphins, enkephalin analogs, morphine sulfate or vehicle were administered intravenously via the tail vein 30 seconds prior to the intraperitoneal administration of 10 mg/kg of 5-HTP or vehicle. β-Endorphin and morphine sulfate, when administered subcutaneously, were given 1 minute prior to 5-HTP administration. In the experiment involving naloxone HCl, it or the vehicle were given 5 minutes prior to the administration of β-endorphin.

The amount of diarrhea produced by 5-HTP was determined as follows. Immediately following the administration of 5-HTP, the mice were individually housed in open-bottomed wire cages of a width and length of 8.5 cm and a height of 7.5 cm, resting on preweighed plastic sheets. The mice were removed from the cages 30 minutes after receiving 5-HTP, and any visible urinary discharge present on the plastic sheet was blotted dry. The sheets were then reweighed. The weight increment was considered to represent fecal weight. Under these conditions, the i.p. administration of 10 mg/kg of 5-HTP consistently produced about a four-fold increase in fecal weight as compared to vehicle-treated mice. Five-HTP administration also resulted in loose and fluid fecal droppings in comparison to the control mice in which the fecal droppings were of a firm consistency.

In the mice, the intraperitoneal administration of 10 mg/kg of 5-HTP resulted in a rapid onset of diarrhea. As shown by the data contained in Table I, intravenously or subcutaneously administered morphine sulfate was effective in preventing this diarrhea. The anti-diarrhea ED50 for morphine sulfate was 0.46 and 1.45 μ moles/kg following intravenous or subcutaneous administration, respectively.

Both met-enkephalin and leu-enkephalin had only weak anti-diarrhea activity when administered intravenously at a dose of 132 μ moles/kg (Table II).

TABLE I

Anti-Diarrhea Activity of [D-Thr$^2$, Δ$^3$Pro$^5$]-Enkephalinamide

| Treatment * (μm/kg) | 5-HTP (mg/kg) | Mean Fecal Wt. (mg) + S.E. | % Inhibition | ED50 μm/kg + S.E. |
|---|---|---|---|---|
| 0 (Vehicle) | 10 | 180.0 ± 22.1 (10)** | — | |
| 24.10 | 10 | 37.9 ± 12.81(10) | 78.9 | |
| 12.05 | 10 | 49.8 ± 14.44(10) | 72.2 | 2.9 ± 1.74 |
| 3.60 | 10 | 80.1 ± 22.43(10) | 55.3 | |
| 1.2 | 10 | 117.3 ± 11.06(10) | 34.6 | |

\* = [D-Thr$^2$, Δ$^3$Pro$^5$]-Enkephalinamide
\*\* = Number in parenthesis refers to number of mice used

| Treatment (μmoles/kg) | % Inhibition of 5-HTP Diarrhea ± S.E. | Anti-Diarrhea ED50 ± S.E. (μmoles/kg) |
|---|---|---|
| Anti-Diarrhea Activity of Intravenously and Subcutaneously Administered Morphine Sulfate in the Mouse | | |
| Morphine Sulfate (iv) | | |
| 0.07 | 9.4 ± 10.0 (10) | 0.46 ± 0.150 |
| 0.22 | 41.2 ± 6.8 (10) | |
| 0.66 | 63.7 ± 9.7 (10) | |
| 1.32 | 67.8 ± 9.0 (10) | |
| 2.64 | 76.8 ± 4.8 (10) | |
| 6.60 | 99.3 ± 0.7 (10) | |
| Morphine Sulfate (sc) | | |
| 0.07 | 0.0 ± 14.7 (10) | 1.45 ± 0.330 |
| 0.22 | 0.0 ± 15.4 (10) | |
| 0.66 | 23.2 ± 10.2 (10) | |
| 1.32 | 59.8 ± 8.2 (10) | |
| 2.64 | 70.0 ± 9.1 (10) | |
| 6.60 | 87.0 ± 6.4 (10) | |
| Anti-Diarrhea Activity of Enkephalins and Human β-Endorphin in the Mouse | | |
| Met-Enkephalin (iv) | | |
| 66 | 21.3 ± 15.9 (10) | >132 |
| 132 | 23.7 ± 9.6 (10) | |
| Leu-Enkephalin (iv) | | |
| 66 | 0.0 ± 13.1 (10) | >132 |
| 132 | 10.4 ± 7.7 (10) | |
| D-Met$^2$-Pro$^5$-Enkephalin-Amide (iv) | | |
| 0.20 | 1.7 ± 13.2 (10) | 1.38 ± 0.310 |
| 0.60 | 32.3 ± 13.4 (10) | |
| 1.20 | 36.9 ± 11.0 (10) | |
| 2.40 | 66.0 ± 7.6 (10) | |
| 4.30 | 88.6 ± 7.7 (10) | |
| Human β-Endorphin (iv) | | |
| 0.43 | 25.6 ± 16.1 (8) | 1.42 ± 0.636 |
| 0.86 | 46.6 ± 16.0 (8) | |
| 1.73 | 58.3 ± 12.6 (8) | |
| 3.46 | 62.2 ± 10.3 (8) | |
| 6.92 | 66.4 ± 8.0 (8) | |
| 13.84 | 92.2 ± 4.8 (8) | |
| Human β-Endorphin (sc) | | |
| 1.0 | 35.3 ± 14.2 (10) | 2.65 ± 1.425 |
| 3.0 | 51.7 ± 9.9 (10) | |
| 6.0 | 61.0 ± 6.9 (10) | |
| 9.0 | 70.3 ± 8.7 (10) | |

Opiate Activity of [D-Thr$^2$, Δ$^3$Pro$^5$]-Enkephalinamide as Measured by Guinea Pig Ileum Assay The opiate activity of [2-D-threonine, 5-(3,4-dehydroproline)]-enkephalinamide was measured according to the method of H. W. Kosterelitz, R. J. Lydon and H. A. Watt, British Journal of Pharmacology, volume 39 (1970), pp. 398-413. The results of the assay are shown in Table II and are compared with the opiate activities for human β-endorphin and Met-enkephaline. As indicated, the relative potency of the subject compound was 330, compared with 25 for Met-enkephaline and 100 for human β-endorphin.

TABLE II

Opiate Activity of Met-Enkephalin Analog in Guinea Pig Ileum Assay

| Synthetic Peptides | IC$_{50}$ (mol/l) | Relative Potency |
|---|---|---|
| β$_h$-EP | 3.1 × 10$^{-8}$ | 100 |
| Met-EK | 12.4 × 10$^{-8}$ | 25 |
| Tyr-D-Thr-Gly-Phe-Δ Pro-NH$_2$ | 0.93 × 10$^{-8}$ | 336 |

What is claimed is:
1. A compound of the formula:

[D-Thr², Δ³Pro⁵]-enkephalinamide

2. A compound of the formula:

Boc-Tyr-D-Thr-Gly-Phe-Δ³Pro-NH₂